US010126237B2

(12) United States Patent
Van Der Zouw

(10) Patent No.: US 10,126,237 B2
(45) Date of Patent: Nov. 13, 2018

(54) INSPECTION APPARATUS AND DEVICE MANUFACTURING METHOD

(71) Applicant: ASML Netherlands B.V., Veldhoven (NL)

(72) Inventor: Gerbrand Van Der Zouw, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 6 days.

(21) Appl. No.: 14/850,917

(22) Filed: Sep. 10, 2015

(65) Prior Publication Data

US 2016/0091422 A1    Mar. 31, 2016

(30) Foreign Application Priority Data

Sep. 26, 2014  (EP) .................................... 14186590

(51) Int. Cl.
| | | |
|---|---|---|
| *G01N 21/47* | (2006.01) | |
| *G01N 21/956* | (2006.01) | |
| *G03F 7/20* | (2006.01) | |

(52) U.S. Cl.
CPC ....... *G01N 21/4738* (2013.01); *G01N 21/956* (2013.01); *G03F 7/70625* (2013.01);
(Continued)

(58) Field of Classification Search
CPC ........... G01N 21/4738; G01N 2201/12; G01N 2201/061; G01N 2201/0636
See application file for complete search history.

(56) References Cited

U.S. PATENT DOCUMENTS 5,796,508 A * 8/1998 Suzuki ................... B41J 2/465
345/84
6,060,224 A * 5/2000 Sweatt ............... G02B 26/0841
250/492.2
(Continued)

FOREIGN PATENT DOCUMENTS

| CN | 102520507 A | 6/2012 |
|---|---|---|
| WO | WO 01/44854 A2 | 6/2001 |
| WO | WO 2013/178422 A1 | 12/2013 |

OTHER PUBLICATIONS

International Search Report directed to App. No. PCT/EP2015/070287, dated Nov. 26, 2015; 3 pages.
(Continued)

*Primary Examiner* — Sang Nguyen
(74) *Attorney, Agent, or Firm* — Sterne, Kessler, Goldstein & Fox P.L.L.C.

(57) ABSTRACT

An inspection apparatus comprises an illumination system (12) for illuminating a target structure with illuminating radiation and a collection system for collecting the illuminating radiation after it has been scattered by the target structure. A programmable spatial light modulator (713) comprises an array of movable mirror elements (742) in a conjugate pupil plane (P'') of the illumination system. Between the array of mirror elements and the target a common optical path is defined forming part of the illumination system and the collection system. Each mirror element is movable between a first position where it reflects illuminating radiation into the common optical path and a second position where it reflects radiation from the common optical path toward a detector (19, 23). Various combinations of illumination aperture and collection aperture can be defined without the light losses associated with beam splitters and transmissive spatial light modulators.

19 Claims, 8 Drawing Sheets

(52) U.S. Cl.
CPC ............... *G03F 7/70633* (2013.01); *G01N 2021/95676* (2013.01); *G01N 2201/061* (2013.01); *G01N 2201/0636* (2013.01); *G01N 2201/12* (2013.01)

(56) References Cited

U.S. PATENT DOCUMENTS

| | | | | |
|---|---|---|---|---|
| 6,504,943 | B1* | 1/2003 | Sweatt | G02B 27/1086 348/169 |
| 6,788,416 | B2* | 9/2004 | Reuter | G01M 11/005 356/445 |
| 7,116,402 | B2* | 10/2006 | Gui | G03F 7/70291 355/53 |
| 7,154,660 | B2* | 12/2006 | Reuter | G01M 11/00 356/445 |
| 7,483,126 | B2* | 1/2009 | Volfman | G01N 21/55 356/124 |
| 7,553,033 | B2* | 6/2009 | Seki | G03B 21/26 353/85 |
| 8,243,285 | B2* | 8/2012 | Fishbaine | G01N 21/8806 356/603 |
| 9,013,680 | B2* | 4/2015 | Fiolka | G03F 7/70116 355/53 |
| 2001/0041843 | A1 | 11/2001 | Modell et al. | |
| 2003/0076571 | A1* | 4/2003 | MacAulay | G02B 21/0028 359/237 |
| 2003/0184843 | A1* | 10/2003 | Moon | G02B 6/262 359/290 |
| 2004/0125361 | A1* | 7/2004 | Riza | G01J 1/4257 356/121 |
| 2005/0243312 | A1* | 11/2005 | Geshwind | G01J 3/02 356/310 |
| 2006/0007436 | A1* | 1/2006 | Kurosawa | G01N 21/47 356/237.4 |
| 2006/0033921 | A1 | 2/2006 | Den Boef et al. | |
| 2006/0066855 | A1 | 3/2006 | Boef et al. | |
| 2007/0279630 | A1 | 12/2007 | Kandel et al. | |
| 2010/0201963 | A1 | 8/2010 | Cramer et al. | |
| 2010/0277708 | A1* | 11/2010 | Fiolka | G03F 7/70208 355/71 |
| 2010/0328655 | A1 | 12/2010 | Den Boef | |
| 2011/0027704 | A1 | 2/2011 | Cramer et al. | |
| 2011/0043791 | A1 | 2/2011 | Smilde et al. | |
| 2011/0069292 | A1 | 3/2011 | Den Boef | |
| 2011/0102753 | A1 | 5/2011 | Van der Kerkhof et al. | |
| 2012/0044470 | A1 | 2/2012 | Smilde et al. | |
| 2012/0123581 | A1* | 5/2012 | Smilde | G03F 7/70483 700/105 |
| 2012/0206729 | A1* | 8/2012 | Seligson | G03F 7/70633 356/445 |
| 2012/0243004 | A1 | 9/2012 | El Gawhary et al. | |
| 2013/0141730 | A1 | 6/2013 | Quintanilha | |
| 2013/0258310 | A1 | 10/2013 | Smilde et al. | |
| 2013/0271740 | A1 | 10/2013 | Quintanilha | |
| 2014/0043460 | A1* | 2/2014 | Hartell | G02B 17/0615 348/79 |
| 2014/0320633 | A1* | 10/2014 | Haugen | G01N 21/956 348/87 |

OTHER PUBLICATIONS

English-Language Abstract of App. Pub. No. CN 102520507 A, published Jun. 27, 2012; 1 page.

International Preliminary Report on Patentability and Written Opinion of the International Searching Authority directed to related International Patent Application No. PCT/EP2015/070287, dated Mar. 28, 2017; 7 pages.

* cited by examiner

INSPECTION APPARATUS AND DEVICE MANUFACTURING METHOD

BACKGROUND

Field of the Invention

The present invention relates to inspection apparatus and methods usable, for example, to perform metrology in the manufacture of devices by lithographic techniques. The invention further relates to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined. These scatterometers are examples of inspection apparatuses, but the present disclosure applies also to other forms of inspection apparatus, such as microscopes.

Examples of known scatterometers include angle-resolved scatterometers of the type described in US2006033921A1 and US2010201963A1. The targets used by such scatterometers are relatively large, e.g., 40 μm by 40 μm, gratings and the measurement beam generates a spot that is smaller than the grating (i.e., the grating is underfilled). In addition to measurement of feature shapes by reconstruction, diffraction based overlay can be measured using such apparatus, as described in published patent application US2006066855A1. Diffraction-based overlay metrology using dark-field imaging of the diffraction orders enables overlay measurements on smaller targets. Examples of dark field imaging metrology can be found in international patent applications US20100328655A1 and US2011069292A1 which documents are hereby incorporated by reference in their entirety. Further developments of the technique have been described in published patent publications US20110027704A, US20110043791A, US2011102753A1, US20120044470A, US20120123581A, US20130258310A, US20130271740A and WO2013178422A1. These targets can be smaller than the illumination spot and may be surrounded by product structures on a wafer. Multiple gratings can be measured in one image, using a composite grating target. The contents of all these applications are also incorporated herein by reference.

As is known, each product and process requires care in the design of metrology targets and the selection of an appropriate metrology 'recipe' by which overlay measurements will be performed. In the known metrology technique, diffraction patterns and/or dark field images of a metrology target are captured while the target is illuminated under desired illumination conditions. These illumination conditions are defined in the metrology recipe by various illumination parameters such as the wavelength of the radiation, its angular intensity distribution (illumination profile) and its polarization. The inspection apparatus includes an illumination system comprising one or more radiation sources and an illumination system for the delivery of the illumination with the desired illumination parameters. In practice, it will be desired that the illumination system can switch between different modes of illumination by changing these parameters between measurements. In the following, the term 'light' will be used for convenience to refer the illuminating radiation, without implying any limitation to visible wavelengths.

In one commercially available apparatus, the illumination system includes an aperture selection device, defining the desired angular distribution of the light. There are several moving parts in the known illumination system, making it sensitive to vibrations and wear. These moving parts include the aperture selection device. Another published patent application US20130141730A1 proposes to generate illumination profiles with customized color and/or polarization distribution. The customized profiles in that case are achieved by switching between different fibers of a fiber bundle. A fiber switching system is provided to couple a fiber with desired color and polarization of light to a fiber delivering light to a specific location in an illumination pupil. Another aperture device may be required in a collection path, with similar considerations.

As an alternative to moving aperture selection devices, some of the above publications mentioned that a programmable spatial light modulator (SLM) such as a deformable mirror array or liquid crystal (LC) transmissive SLM can be used also. In principle, such devices should enable a more compact design with fewer moving parts. However, in practice these devices have not been implemented for the illuminator. One reason for this may be that providing reflective programmable SLMs such as DMDs in the illumination path requires convoluted beam paths and cause layout difficulties. A problem with LC shutter type devices is that they generally deliver only one polarization of light, while metrology applications require freedom to control polarization as an illumination parameter in the recipe.

A problem in known designs is that one or more beam splitting elements are normally used to deliver and/or collect the inspection radiation. Up to half of the available radiation may be lost at each beam splitter. Therefore measurements are taken with low light intensity, from which it is difficult to obtain low-noise measurements with high throughput. Liquid crystal-type SLMs additionally block at least half of the usable light, adding to this difficulty. US20070279630 (KLA) discloses an 'order selected' microscope for overlay metrology in semiconductor manufacturing. It is said that a spatial light modulator (SLM) device can be provided in one or both of an illumination path and an imaging path. Examples of SLM include chrome-on-glass patterns, and may provide an apodization function, rather than selection. For the imaging path, it is mentioned that a liquid crystal transmissive or reflective pixellated element or a DMD (digital micro-mirror device) may be used. However, this is not mentioned for the illumination path, and polarization as an illumination parameter is not discussed at all.

SUMMARY OF THE INVENTION

The present invention aims to provide alternative illumination systems for metrology and other applications in which an illumination profile can be selected by a programmable device, without some of the compromises that would otherwise result. For example, the invention may improve utilization of radiation to allow improved measurement speed and/or measurement performance.

The invention in a first aspect provides an inspection apparatus comprising:—
an illumination system for illuminating a target structure with illuminating radiation;
a collection system for collecting the illuminating radiation after it has been scattered by the target structure; and
a programmable spatial light modulator that forms part of both the illumination system and the collection system, the spatial light modulator comprising an array of movable reflective elements and being operable to define simultaneously a spatial profile of the illuminating radiation and a spatial profile of collection of the scattered radiation.

In some embodiments of the invention, an objective lens forms part of both the illumination system and the collection system. The array of movable reflective elements may for example be provided in a plane conjugate with a pupil plane of the objective lens.

In the collection system, an image detector may be provided, to capture the collected radiation, or a portion of it, for digital processing. The detector may be provided in another plane conjugate with the pupil plane of the objective lens. This detector can be used for angle-resolved scatterometry, for example. Alternatively or in addition, an image detector may be provided in a field plane of the objective lens. This image detector can be used for forming an image of the target using selected portions of the scattered radiation. Detectors may be provided in both a conjugate pupil plane and a conjugate field plane. In an inspection apparatus having the form of a microscope, an eyepiece may be included for observing the collected scattered radiation, instead of or as well as a digital image detector.

In some embodiments of the invention, each element in the array of reflective elements is movable between at least a first position and a second position. Reflective elements that are in the first position define active portions of the spatial profile of the illuminating radiation while elements that are in the second position define active portions of the spatial profile of collection. This array of movable elements may comprise a commercially available DMD device, for example.

The invention in a second aspect provides a method of inspection of a target structure comprising:
illuminating a target structure with illuminating radiation;
collecting the illuminating radiation after it has been scattered by the target structure;
using a programmable spatial light modulator that comprises an array of movable mirror elements to define simultaneously a spatial profile of the illuminating radiation and a spatial profile of collection of the scattered radiation.

The method may include collecting scattered radiation a plurality of times from the same target structure, changing the spatial profiles each time, and/or collecting scattered radiation from a plurality of target structures, using different spatial profiles for different target structures.

The invention in another aspect provides a method of manufacturing devices wherein a device pattern is applied to a series of substrates using a lithographic process, the method including:
using an inspection apparatus or method according to the first or second aspect of the invention to measure a property of at least one structure of interest formed on at least one of said substrates, and
controlling the lithographic process for later substrates in accordance with the measured property.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
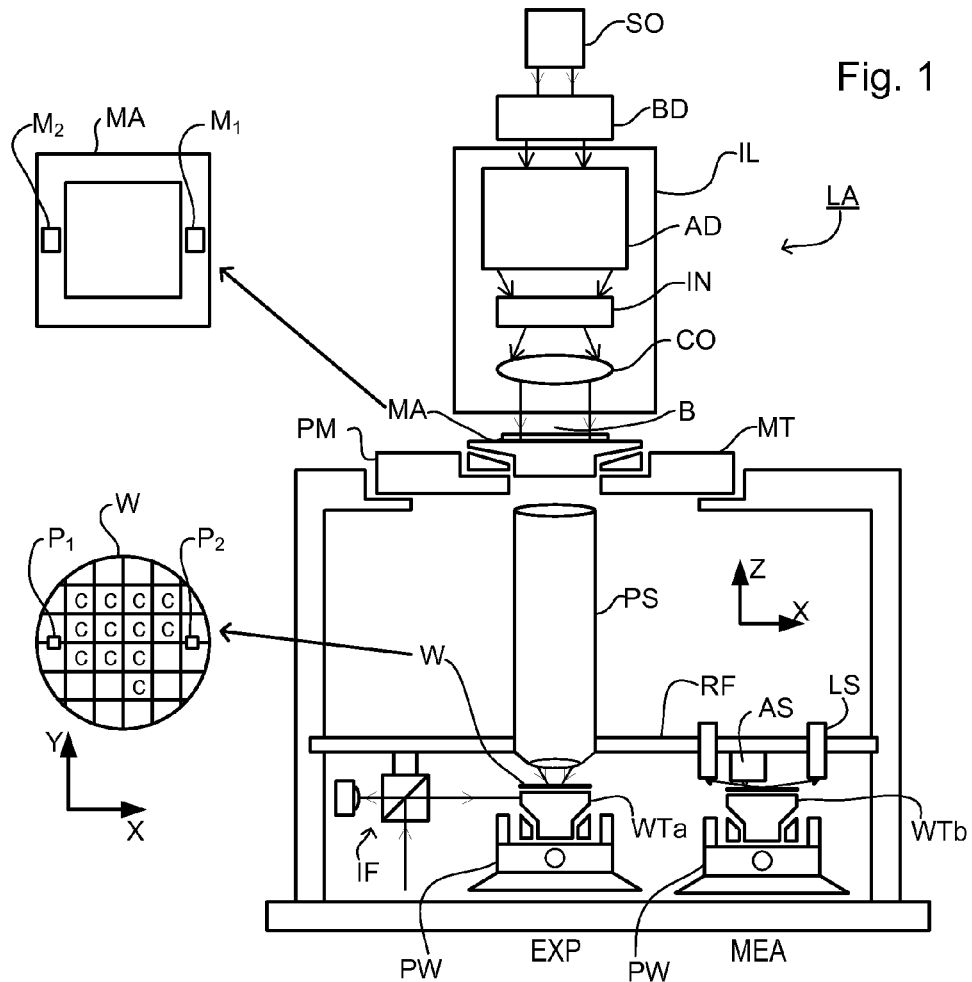
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can take many forms, The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment marks may also be included within dies, in amongst the device features, in which case it is desirable that the markers be as small as possible and not require any different imaging or process conditions than adjacent features.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
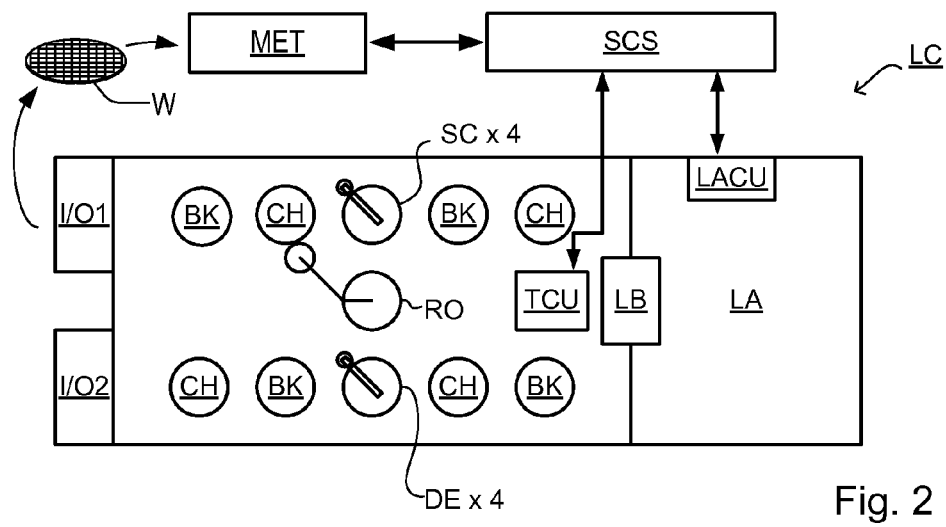
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc.

Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
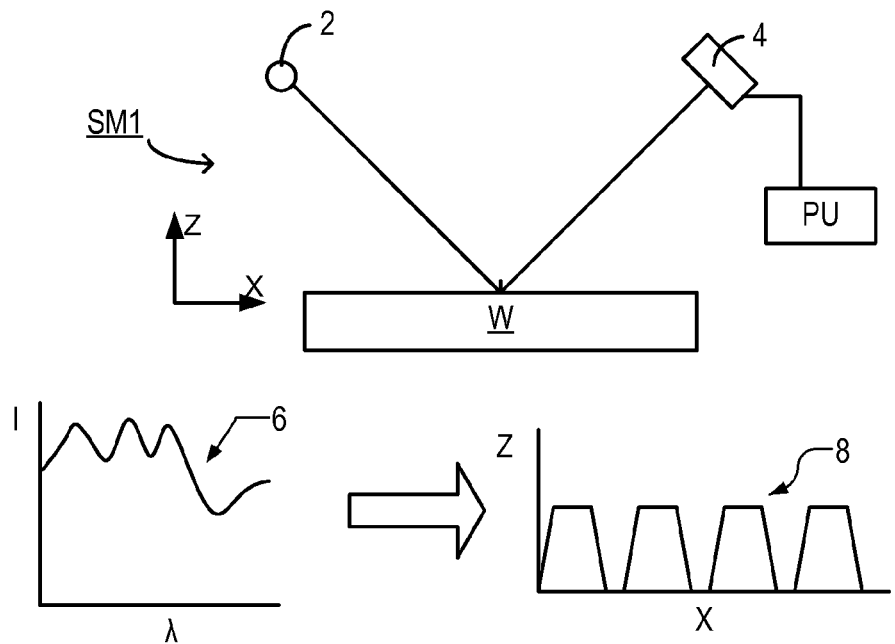
FIG. 3 illustrates the principles of operation of a spectroscopic scatterometer as a first example of an inspection apparatus.

FIG. 3 depicts a known spectroscopic scatterometer which may be used as an inspection apparatus in a metrology system of the type described above. It comprises a broadband (white light) radiation projector 2 which projects radiation onto a substrate W. The reflected radiation is passed to a spectrometer 4, which measures a spectrum 6 (intensity as a function of wavelength) of the specular reflected radiation. From this data, the structure or profile 8 giving rise to the detected spectrum may be reconstructed by calculation within processing unit PU. The reconstruction can be performed for example by Rigorous Coupled Wave Analysis and non-linear regression, or comparison with a library of pre-measured spectra or pre-computed simulated spectra. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
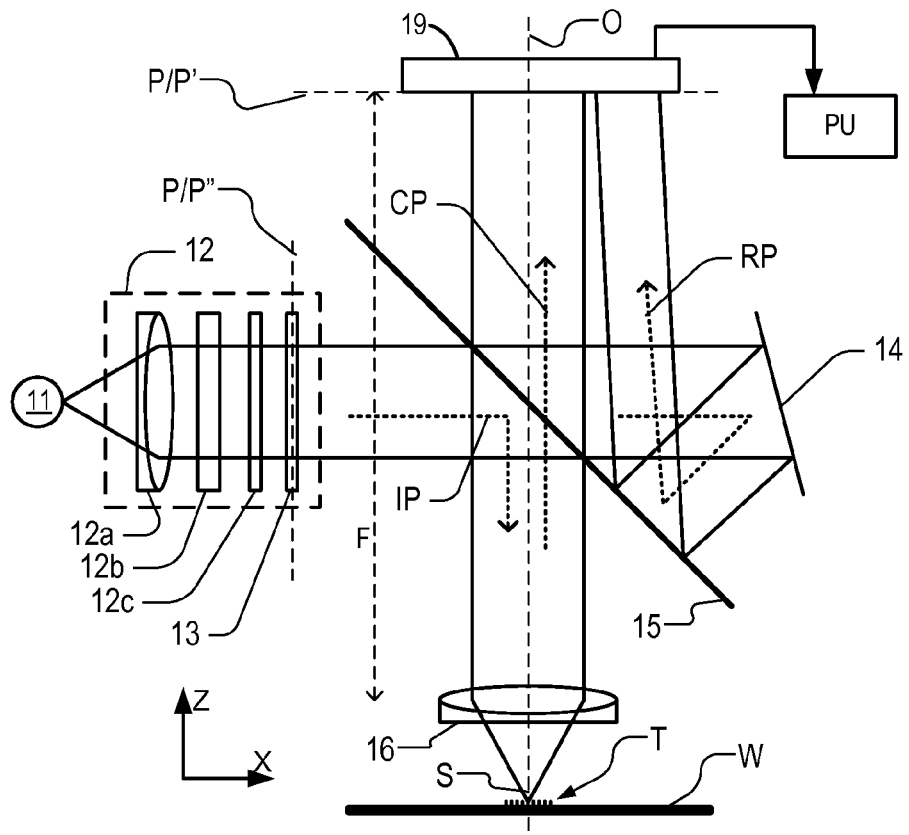
FIG. 4 illustrates in schematic form an angle-resolved scatterometer as another example of an inspection apparatus.

FIG. 4 shows the basic elements of a known angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired.

As in the lithographic apparatus LA, one or more substrate tables may be provided to hold the substrate W during measurement operations. The substrate tables may be similar or identical in form to the substrate tables WTa, WTb of FIG. 1. (In an example where the inspection apparatus is integrated with the lithographic apparatus, they may even be the same substrate tables.) Coarse and fine positioners may be configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. It is convenient to think and describe operations as if the objective lens and optical system being brought to different locations on the substrate, when in practice the optical system remains substantially stationary and only the substrate moves. Provided the relative position of the substrate and the optical system is correct, it does not matter in principle whether one or both of those is moving in the real world.

When the radiation beam is incident on the beam splitter 16 part of it is transmitted through the beam splitter (partially reflecting surface 15) and follows a reference path RP towards a reference mirror 14.

Radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and may instead be re-imaged with auxiliary optics (not shown) onto the detector located in a so-called conjugate pupil plane P'. The detector may be a two-dimensional detector so that a two-dimensional angular scatter spectrum or diffraction spectrum of a substrate target 30 can be measured. In the pupil plane or conjugate pupil plane, the radial position of radiation defines the angle of incidence/departure of the radiation in the plane of focused spot S, and the angular position around an optical axis O defines azimuth angle of the radiation. The detector 19 may be, for example, an array of CCD or CMOS sensors, and may use an integration time of, for example, 40 milliseconds per frame.

Radiation in reference path RP is projected onto a different part of the same detector 19 or alternatively on to a different detector (not shown). A reference beam is often used for example to measure the intensity of the incident radiation, to allow normalization of the intensity values measured in the scatter spectrum.

It may be noticed that radiation is reflected by and later transmitted through partially reflecting surface 15 on its way from source 11 to detector 19. At each reflection or transmission, a substantial portion of the radiation is "lost" and cannot be used in the measurement. The amount lost is typically 50% at each encounter with the surface. Therefore in the arrangement shown, the maximum available radiation is only 25% of the illuminating radiation, This is in addition to any losses for polarization (another 50%), spectral filtering and the like, A portion of the lost radiation may be used for other purposes, for example to serve for focusing or alignment; or for the reference beam as described above. However, this loss of usable signal inevitably limits the performance of the inspection apparatus, in terms of accuracy and/or throughput. Further below we disclose an alternative arrangement which seeks to make more of the radiation usable in measurements.

Returning to the known apparatus, the various components of illumination system 12 can be adjustable to implement different metrology 'recipes' within the same apparatus. Color filter 12b may be implemented for example by a set of interference filters to select different wavelengths of interest in the range of, say, 405-790 nm or even lower, such as 200-300 nm. An interference filter may be tunable rather than comprising a set of different filters. A grating could be used instead of interference filters. Polarizer 12c may be rotatable or swappable so as to implement different polarization states in the radiation spot S. Aperture device 13 can be adjusted to implement different illumination profiles. Aperture device 13 is located in a plane P''' conjugate with pupil plane P of objective lens 16 and the plane of the detector 19. In this way, an illumination profile defined by the aperture device defines the angular distribution of light incident on substrate radiation passing through different locations on aperture device 13.

The detector 19 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic-polarized light and transverse electric-polarized light.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS. Illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes. The techniques disclosed herein are not limited to inspection of grating structures, and any target structure, including a blank substrate or a substrate having only flat layers on it, is included within the term "target structure"

In addition to measurement of parameters by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement using the instrument of FIG. 3 or 4 are described for example in published patent application US2006066855A1 cited above. Simply stated, while the positions of the diffraction orders in the diffraction spectrum of the target are determined only by the periodicity of the target, asymmetry of intensity levels in the diffraction spectrum is indicative of asymmetry in the individual features which make up the target. In the instrument of FIG. 4, where detector 19 may be an image sensor, such asymmetry in the diffraction orders appears directly as asymmetry in the pupil image recorded by detector 19. This asymmetry can be measured by digital image processing in unit PU, and calibrated against known values of overlay.

FIG. 5(a) shows in more detail an inspection apparatus implementing angle-resolved scatterometry by the same principles as the apparatus of FIG. 4, with additional adaptations for performing so-called dark field imaging. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating T and diffracted rays are illustrated in more detail in FIG. 5(b).

The same reference numbers are used for components described already in the FIG. 4 apparatus. The illumination path is labeled IP as before. The reference path RP is omitted, for clarity. Compared with that apparatus, a second beam splitter 17 divides the collection path into two branches. In a first measurement branch, detector 19 records a scatter spectrum or diffraction spectrum of the target exactly as described above. This detector 19 may be referred to as the pupil image detector.

It may be noted at this point how the second beam splitter 17 further divides the amount radiation, effectively halving the amount of radiation that is usable for measurements in each branch. The present disclosure does not intend to exclude the use of beam splitters and partially reflecting surfaces. However, the need or desire for a commercial apparatus to provide multiple functions using different optical branches illustrates that substantial loss of usable signal occurs in any path between source and detector.

In the second measurement branch, imaging optical system 22 forms an image of the target on the substrate W on sensor 23 (e.g. a CCD or CMOS sensor). An aperture stop 21 is provided in a plane that is in the collection path in a plane conjugate to the pupil-plane (it may also be called a pupil stop). Aperture stop 21 can take different forms, just as the illumination aperture 13 can take different forms. Typically, aperture stop 21 functions to block the zeroth order diffracted beam so that the image of the target formed on sensor 23 is formed only from the first order beam(s). This is the so-called dark field image, equivalent to dark field microscopy. The images captured by sensors 19 and 23 are output to image processor and controller PU, the function of which will depend on the particular type of measurements being performed.

In the illumination path in this example, additional optics are shown such that a field stop 13' can be placed in a plane conjugate with the plane of the target and the image sensor 23. This plane may be referred to as a field plane, or conjugate image plane, and has the property that each spatial position across the field plane corresponds to a position across the target. This field stop may be used for example to shape the illumination spot for a particular purpose, or simply to avoid illuminating features that are within the field of view of the apparatus but not part of the target of interest. The following drawings and discussion refer, by way of example, to techniques for implementation of the function of aperture device 13, but the present disclosure also encompasses use of the same techniques to implement the function of field stop 13'.

Figure 6:
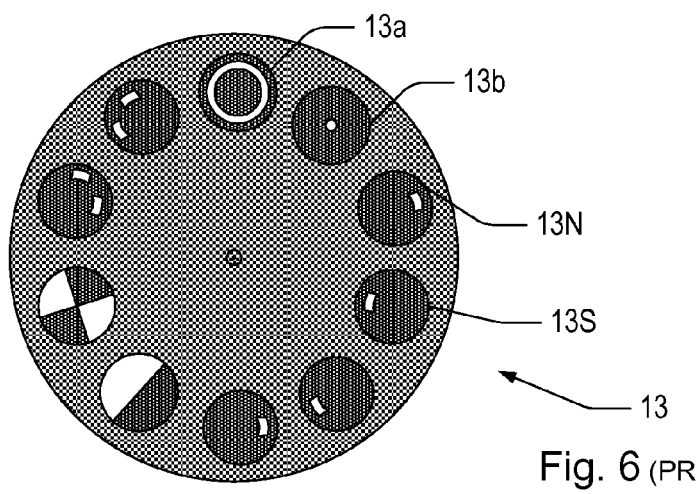
FIG. 6 illustrates schematically an aperture device used in the illumination system of a known inspection apparatus.

FIG. 6 shows an example aperture device 13. This takes the form of a wheel, in which a variety of apertures 13a, 13b, 13N, 13S can be selected and positions in the beam path of illumination system 12. As already mentioned, the angular range at which the radiation is incident on the substrate can be selected by defining a spatial intensity distribution in a plane that presents the spatial spectrum of the substrate plane, here referred to as a (conjugate) pupil plane. In particular, this can be done conventionally by selecting an aperture of suitable form in the path of collimated radiation coming from lens 12a.

Using, for example, aperture 13a, we obtain an annular illumination profile, centered on the optical axis of the illumination system. The radiation in measurement spot S will be incident on substrate W in a cone of angles not encompassing the normal to the substrate. In other words, the aperture 13a can be used to provide an off-axis illumination profile.

In the language of the introduction and claims, we can say that the spatial profile of illumination can be defined by an aperture device. When the aperture device is located in a plane conjugate with a pupil plane of an illumination optical system, the aperture device may specifically define an angular illumination profile. (A field stop 13', on the other hand, defines the spatial profile of illumination across the plane of the target.)

As shown in more detail in FIG. 5(b), target grating T is placed with substrate W normal to the optical axis O of objective lens 16. In the case of an off-axis illumination profile, A ray of illumination I impinging on grating T from an angle off the axis O gives rise to a zeroth order ray (solid line 0) and two first order rays (dot-chain line+1 and double dot-chain line −1). It should be remembered that with an overfilled small target grating, these rays are just one of many parallel rays covering the area of the substrate including metrology target grating T and other features. Since the annular aperture 13a in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Other modes of illumination are possible by using different apertures. For example, aperture 13b provides on-axis illumination. Apertures 13N (north') and 13S (south') each provide off-axis illumination from a specific narrow range of angles only. Returning to FIG. 5(a), this is illustrated by designating diametrically opposite portions of the annular aperture as north (N) and south (S). The +1 diffracted rays from the north portion of the cone of illumination, which are labeled +1(13N), enter the objective lens 16, and so do the −1 diffracted rays from the south portion of the cone (labeled −1(13S)). As described in the prior applications mentioned in the introduction, using the dark-field imaging sensor 23 while switching between apertures 13N, 13S of this type is one way of obtaining asymmetry measurements from multiple small targets. Aperture stop 21 can be used to block the zeroth order radiation when using off-axis illumination.

While off-axis illumination is shown, on-axis illumination of the targets may instead be used and an aperture stop 13b with an off-axis aperture is used to pass substantially only one first order of diffracted light to the sensor. In one example, prisms are used in place of aperture stop 21 which have the effect of diverting the +1 and −1 orders to different locations on sensor 23 so that they can be detected and compared without making two images. This technique, is disclosed in the above-mentioned published patent application US2011102753A1, the contents of which are hereby incorporated by reference. 2nd, 3rd and higher order beams (not shown in FIG. 5) can be used in measurements, instead of or in addition to the first order beams.

Illumination profiles can be varied greatly and the use of custom illumination is becoming more and more important in both lithography and optical metrology. The customization of the illumination enables improvement of the measurement quality (TMU, cross-correlation and sensitivity). Just a few examples of illumination profiles are shown in the 'aperture wheel' FIG. 6. For reasons of space, it is difficult to include all the possibly desirable apertures in one wheel. Also, the mechanism required to change apertures introduces potential positioning errors and vibration sources, as well as delays in operation. Consequently there is a desire to implement illumination modes using programmable spatial light modulators (SLMs). Various technologies are available for use as programmable SLMs, of which the best-known are liquid crystal (LC) shutters and micromirror arrays (also known as deformable micromirror devices or DMDs). LC shutters have drawbacks for use as aperture device 13 in the illustrated apparatus, including loss of an additional 50% of the usable light and restrictions on polarization.

Figure 5:
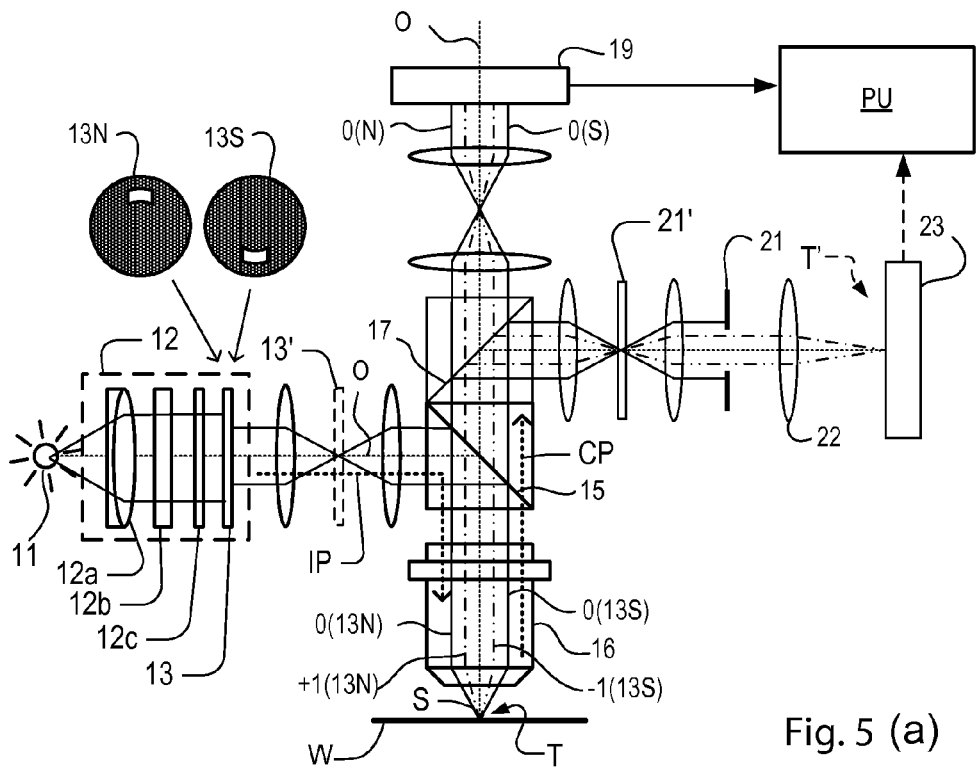
FIGS. 5(a) and 5(b) illustrate schematically an inspection apparatus adapted to perform angle-resolved scatterometry and dark-field imaging inspection methods.
Figure 5:
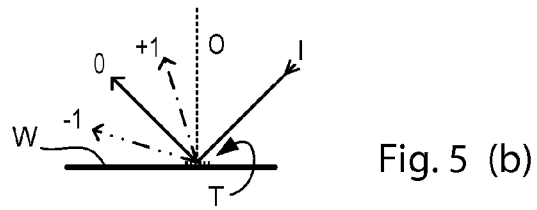

An array of movable reflective elements such as a DMD is, in principle, very attractive as an alternative to LC shutter-type SLMs. DMDs with thousands of pixels and high switching speeds are readily available, being used for example in digital projectors. Depending on the reflective material, reflective SLMs need not restrict the usable polarizations. Also light loss can be minimal. However, reflective SLMs require convoluted layouts. To design a compact optical layout for a real commercial inspection apparatus, which is shown greatly simplified in FIG. 5, is already challenging in view of the different branches and auxiliary functions that must be included. To include one or more reflective SLMs in each branch greatly increases the challenge.

The present disclosure enables the benefits of programmable SLMs to be obtained in an inspection apparatus such as a scatterometer, while improving light utilization and maintaining a compact layout.

Figure 7:
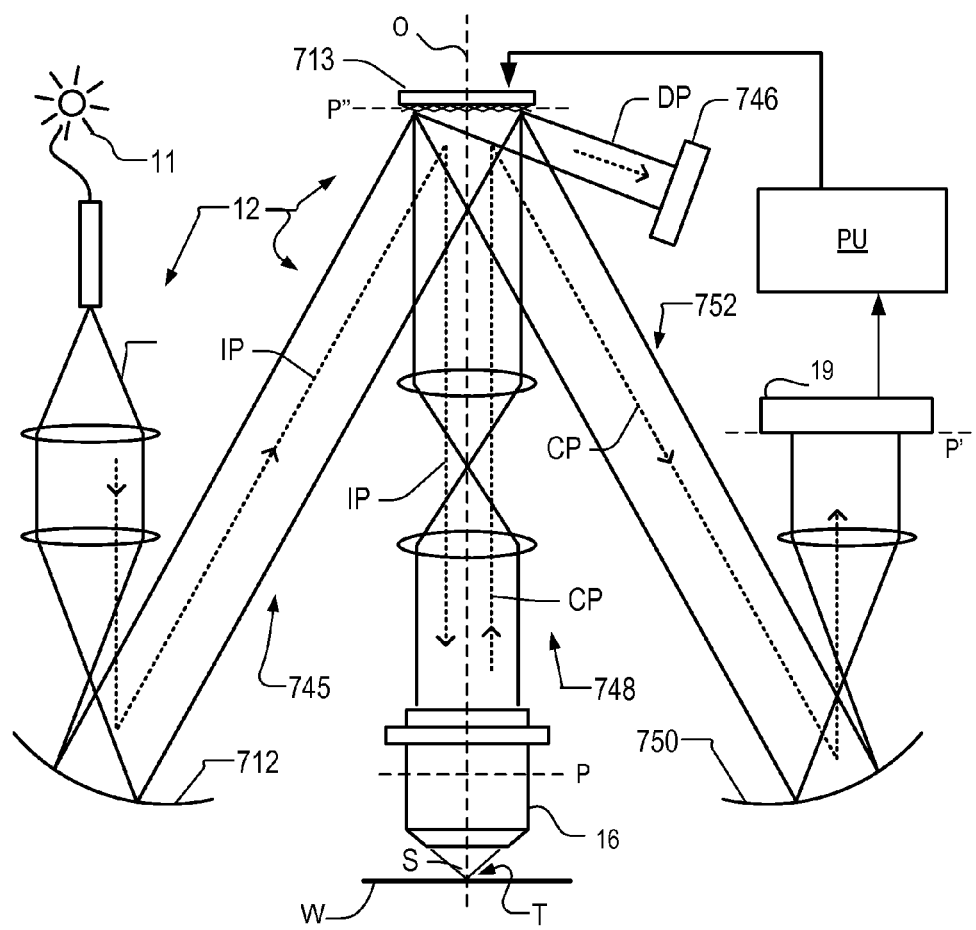
FIG. 7 (a) is a schematic view of an inspection apparatus adapted to perform angle-resolved scatterometry according to a first embodiment of the present invention with (b) detail of a mirror array device used in the apparatus.
Figure 7:
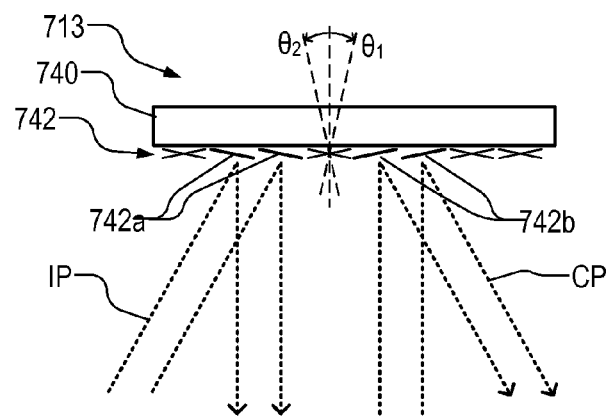

FIG. 7 (a) shows a general arrangement of an inspection apparatus, in which components having the same functions as in the apparatus of FIGS. 4 and 5 have similar reference signs. Thus we see a radiation source 11, and an objective lens 16, all delivering a spot S of illuminating radiation to a target T. These components, together with associated lens systems shown schematically, may be considered as an illumination system 12 in the language of the introduction and claims. They define an illumination path IP. There is also a collection system that defines a collection path CP for radiation scattered by the target. The collection system will be described further below.

In the example illustrated, illumination path IP is folded by the inclusion of a mirror 712 in illumination system 12. This mirror is not essential, but assists in achieving a compact arrangement. The mirror 712 is curved in this example, performing a collimating function. The mirror need not be curved, and the collimating function could be performed by a refractive lens. However, because of the oblique angle of incidence on the DMD, it is simpler to achieve the required optical corrections with reflective element.

In the illumination path IP, a programmable, reflective spatial light modulator is provided in the form of a mirror array device 713. This device folds the path again, while serving the function of aperture stop 13. The mirror array device is positioned in a plane P'' which is conjugate with pupil plane P of the objective lens. In particular, the mirror array device is controlled by processor PU to act as a programmable spatial light modulator. Processor PU thus functions as the controller in the language of the claims, in addition to calculating the results of measurements and other functions. The controller function can be separated from the processor function, provided that the processor knows which spatial profiles have been used to obtain measurement data being used in a calculation.

As illustrated in more detail in FIG. 7(b), movable mirror array device 713 comprises a substrate 740 on which is arranged an array 742 of individually movable reflective elements. These reflective elements will be referred to as mirror elements in the following description. A row of eight mirror elements is shown, purely for illustration. In practice a two-dimensional array of hundreds or thousands of miniature mirrors may be envisaged. Each mirror element in this example can be set in one of two predetermined positions. Setting a first position places the mirror element at a first orientation represented by angle θ1 and setting a second position places the mirror element at a second orientation represented by angle θ2. In a commercially available DMD, for example, angle θ1 may be 12 degrees, while angle θ2 is −12 degrees, relative to direction a normal to the plane of the array 742.

The section of the illumination path IP which leads from folding mirror 712 to mirror array device 713 may be regarded as an illumination input path 745 in the illumination system 12. As illustrated in FIG. 7(b), mirror elements 742a placed at angle θ1 (first position) will reflect radiation from the input path into the common optical path, and so toward objective lens 16 and the target. Further, only those elements that are in the first position will define active (bright) portions in the spatial profile of the illumination system. Mirror elements at angle θ2 will not. A beam dump 746 collects the illuminating radiation reflected by these elements, which follow a dump path DP as shown. Beam dump 746 may be a simple absorber. However, if desired, sensing functions can be performed with the dump path, for example for intensity normalization, so that the light here is not wasted.

Regarding the mirror elements as pixels viewed from the perspective of the objective lens, mirror elements 742a lying at angle θ1 would appear as bright pixels. These pixels represent active portions in the spatial profile of the illumination system. Mirror elements 742b lying at angle θ2 will appear dark.

In the illustrated example, only a few movable mirror elements (pixels) are shown, for the sake of clarity. The number of pixels (movable reflective elements) in a real implementation is of course a matter of design choice. There may be several hundred or many thousands of pixels in practice. For example, it may be convenient to provide a number of pixels in each path that is equal or substantially equal to the number of pixels in the pupil image sensor 19 of the inspection apparatus. In this way, spatial resolution in the illumination profile can match the spatial resolution in the pupil image sensor. For example there may be 500×500 pixels in each part of SLM 260 and 500×500 pixels in pupil image sensor 19. DMD devices with greater numbers of pixels are readily available, including the well-known DLP range of products from Texas Instruments, Dallas, Tex., USA (www.dlp.com).

Returning to FIG. 7(a), we consider now the collection system for radiation that has been scattered by target T and contains useful information for measuring properties of the target. As in the known apparatus, a collection path is provided for collecting scattered radiation and delivering it to detector 19. As in the known instrument, the illumination path IP and collection path CP share objective lens 16 and other components. In the present apparatus, also the programmable SLM formed by mirror array device 713 is also part of the collection path. In other words, between the array of mirror elements and the target a common optical path 748 is defined forming part of the illumination system and the collection system. These common elements, along with detector and associated lenses, form the collection system in the language of the introduction and claims. In a manner similar to the illumination system, the collection system in this example includes a folding mirror 750. Mirror 750 is curved, so as to perform a focusing function. In the case of the pupil image sensor 19, this sensor lies in a conjugate plane P' of the pupil plane P of objective lens 16. The collection system includes mirror 750 and other focusing elements for forming an image of the programmable SLM in conjugate pupil plane P''' onto sensor 19 in conjugate pupil plane P'. (In an embodiment having an imaging branch and field image sensor 23, an image of the target T would be formed, as already described above.)

Referring again to FIG. 7(b), it will be seen that the geometric layout of the optical paths and the angles of the set positions of mirror elements in mirror array device 740 have been designed so that mirror elements 742b lying at angle θ2 will reflect radiation returning from objective lens 16 into an output path 752 that leads to sensor 19. That is to say, under control of processor PU, each mirror element of the mirror array 742 can serve at different times as part of the illumination path IP or part of the collection path. By this compact arrangement, many useful spatial profiles can be programmed for the illumination system and the collection system. It is a constraint that the same element cannot serve simultaneously in both the illumination path and the collection path. However, as will be illustrated below, this constraint does not undermine the benefits of the arrangement in practical applications such as semiconductor metrology.

Now, it may be noted that, in the apparatus of FIG. 7, neither the illumination path IP nor the collection path CP includes a partially reflecting surface 15. Consequently the proportion of radiation usable at the detector 19 can be up to four times what it is in the known apparatus. As mentioned already, the present disclosure in no way excludes the use of partially reflecting surfaces, where it may be useful to divide the usable radiation into different paths for different functions. For example, a second detection branch with dark field imaging sensor 23 may be provided using a beam splitter 17 (not shown; similar to that in FIG. 5). However, eliminating the partially reflecting surface 15 and using a high-efficiency array of reflective elements immediately increases the efficiency of utilization of the available radiation and the available time.

Because the illumination path is twice folded, the collection path is twice folded and a reflective SLM is shared between the two paths, a compact design is achieved.

Figure 8:
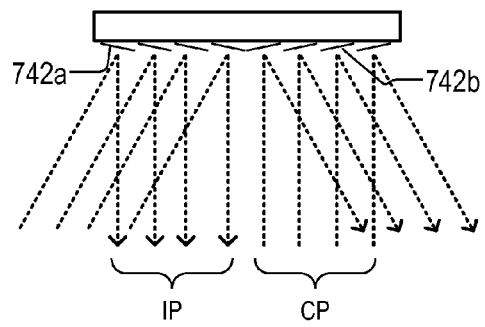
FIG. 8 shows the mirror array device of FIG. 7 in three configurations FIGS. 8(a) to 8(c), and two further configurations FIGS. 8(d) and 8(e) illustrating embodiment of the invention that may be implemented using modified mirror array devices.
Figure 8:
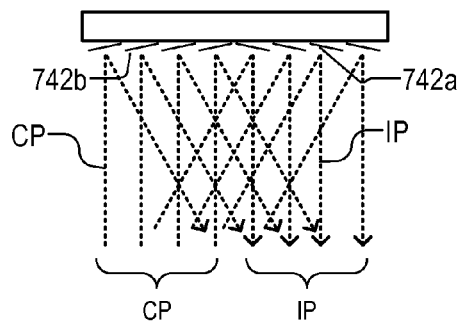
Figure 8:
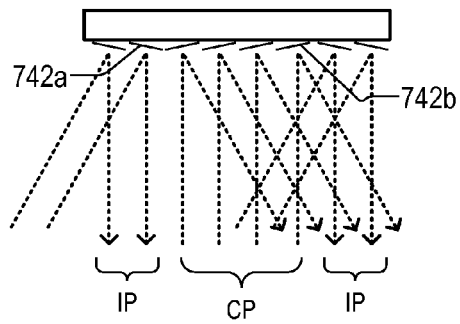
Figure 8:
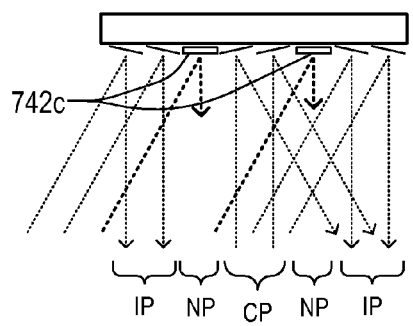
Figure 8:
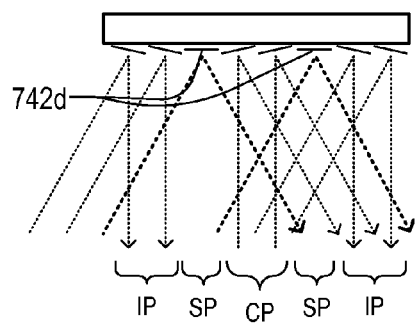

FIG. 8 shows how programming various configurations of the mirror array device can implement the different kinds of spatial profiles for illumination and collection that are used in the known scatterometry techniques. (Applications are not limited to scatterometry, and may for example include microscopy). It will be understood that the array is illustrated in one arbitrary cross-section, and two-dimensional patterns are set in practice. All the different configurations are set by application of suitable control signals from a controller such as processor PU.

At (a) in FIG. 8, mirror elements 742a in the left half of the array are in the first position, so that the left half of the pupil is active (bright) in the illumination path IP. Mirror elements 742b in the right half of the array are in the second position so that the right half of the pupil is active in the collection path CP. Referring also to FIG. 5(b), the skilled reader will appreciate that zero order (reflected) radiation from the target will be received at detector 19.

At (b) in FIG. 8 the positions of the mirror elements are simply the reverse of configuration (a). Mirror elements 742a in the right half of the array are in the first position, so that the right half of the pupil is active (bright) in the illumination path IP. Mirror elements 742b in the left half of the array are in the second position so that the left half of the pupil is active in the collection path CP. Again, zero order (reflected) radiation from the target will be received at detector 19.

In configuration (c), mirror elements 742a in outer regions of the array are in the first position, so that outer portions of the pupil are active in the illumination path IP. This gives off-axis illumination profile. Mirror elements 742b in a central portion of the array are in the second position, so that a central portion of the pupil is active in the collection path CP. As in the set-up of FIG. 5(a), off-axis illumination is provided, effectively an on-axis aperture stop (21 in FIG. 5). By reversing the set positions, on-axis illumination with off-axis collection can equally easily be arranged.

FIG. 8(d) shows an example configuration that can be implemented if the mirror array device allows a third position to be set for each mirror element. Although this is a two-dimensional illustration, it will be appreciated that light rays can be deflected both into an out of the plane of the drawing. In a practical apparatus, the beam paths, especially if branched for various purposes, are likely to be three-dimensional. In the illustrated example (d), elements 742c are in a third position whose tilt axis includes a component parallel to the page. Therefore in this third position and element deflects radiation into or out of the plane of the drawing, that is away from the common optical path. These elements are therefore active in neither the illumination path nor the collection path. These inactive portions of the pupil are labeled NP ("no path"). As in the case of the dump path DP, the deflected radiation can be sent to an absorber (beam dump), or used for a useful purpose.

A mirror array with three positions is not so readily available, but can be custom made if required. Note that the third position need not be as accurately defined as the first and second positions, if its purpose is only to dump unwanted radiation. A benefit of this configuration is that it allows modes in which areas of the pupil are active in neither the illumination system nor the collection system. Although a position deflecting radiation out of the plane of the paths IP, CP is shown, a "no path" position more extreme than either the first position or the second position may be provided instead.

FIG. 8 (e) shows an example configuration that can be implemented if the mirror array device allows a different third position to be set for each mirror element. In this case, elements 742d are shown in a third position that is exactly half way between the first position and the second position.

Consequently such elements provide a path that leads directly from the input path of the SLM to the output path, omitting entirely the common optical path, the objective lens 15 and the target T. Zones where elements are in this position are labeled SP ("straight through" path). Such a path can be useful for example to obtain reference signals for calibration. The "straight through" path can be used at times when measurements are not being performed. It can also be used at the same time as measurements are being performed, but in portions of the pupil that are not involved Again, a mirror array with three well-defined positions is not so readily available, but can be custom made if required. If it can be made, a mirror array with four positions could be used to implement the features of configuration (d) and (e) in the same apparatus. Also, while mirror arrays having third and fourth positions are not necessarily easy to make in the form of micromirror devices fabricated by lithography, the invention is not limited to micromirror devices. An array of larger mirror elements, moveable by more conventional means, may be envisaged.

Figure 9:
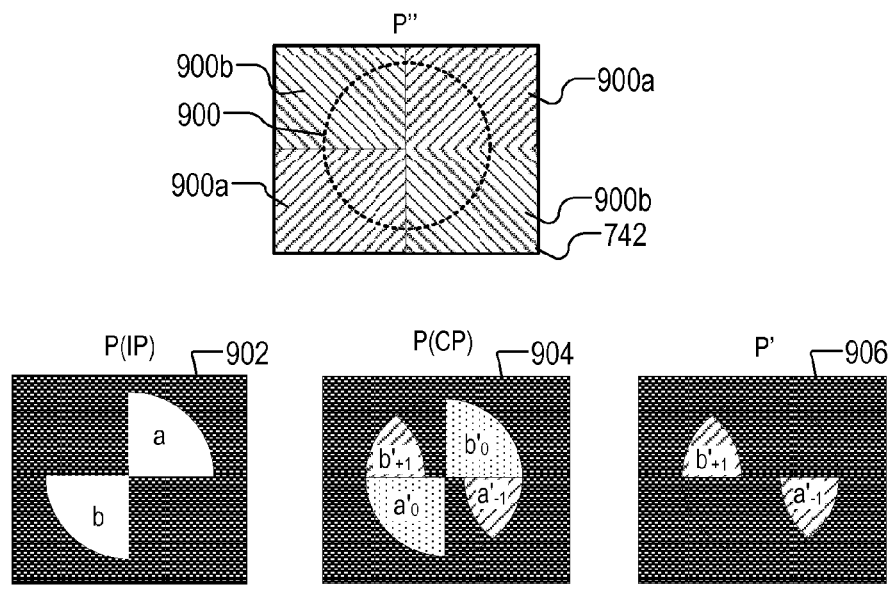
FIG. 9 illustrates in more detail operation of the apparatus of FIG. 7 in one example configuration of the mirror array device.

Referring to FIG. 9, and viewing the mirror array 742 in two dimensions, a circle 900 represents the pupil of the illumination system and collection system. Mirror array is rectangular simply because this is convenient and readily available. Many thousands of pixels are present, and not shown individually. Portions of the array outside the pupil 900 are inactive. (The two pupils need not be identical in extent, but we assume for simplicity that they are.) Suppose that a specific spatial profile of illumination is desired, illustrated at 902. In this desired spatial profile of the illumination system, two diametrically opposite quadrants, labeled a and b, are bright, while the other two quadrants are dark (opaque). This type of aperture is known in scatterometry apparatus, from the published patent application US 2010/201963. The merits of this modified illumination aperture will be described further below.

To implement this segmented illumination profile, mirror elements in portions 900a or the array 742 are set to the first position and mirror elements 900b are set to the second position. Now assume that the target T is a one-dimensional diffraction grating. While the spatial profile 902 of the illumination has bright quadrants labeled a and b, the diffraction pattern resulting from diffraction by the lines of the target grating is represented by the pattern at 904. In this pattern, in addition to zero order reflections labeled a0 and b0 there are first order diffraction signals visible, labeled a−1, a+1, b−1 and b+1. Because other quadrants of the illumination aperture are dark, and more generally because the illumination pattern has 180° rotational symmetry, the diffraction orders a−1 and b+1 are "free" meaning that they do not overlap with the zero order or higher order signals from other parts of the illumination aperture. This property of the segmented illumination pattern can be exploited to obtain clear first order signals from a diffraction grating (alignment mark) having a pitch which is half the minimum pitch that could be imaged if a conventional, circularly-symmetric illumination aperture were used.

Recall that portions 900b of the mirror array 742 are active in the collection path CP. As seen at 906, these free active portions include the parts of the pupil where the free first orders of the diffraction pattern 904. In contrast to the conventional scatterometer, the zero order portions are not visible because the array portions 900a cannot be active in both the illumination path and the collection path at the same time. However, if the purpose of the measurement is to study the first order diffraction (for example to measure target asymmetry or overlay), then this is no loss. As mentioned already in relation to FIG. 8 configurations (a) and (b), zero order scattered radiation can be collected, by arranging a configuration which is does not have 180° rotational symmetry.

Figure 10:
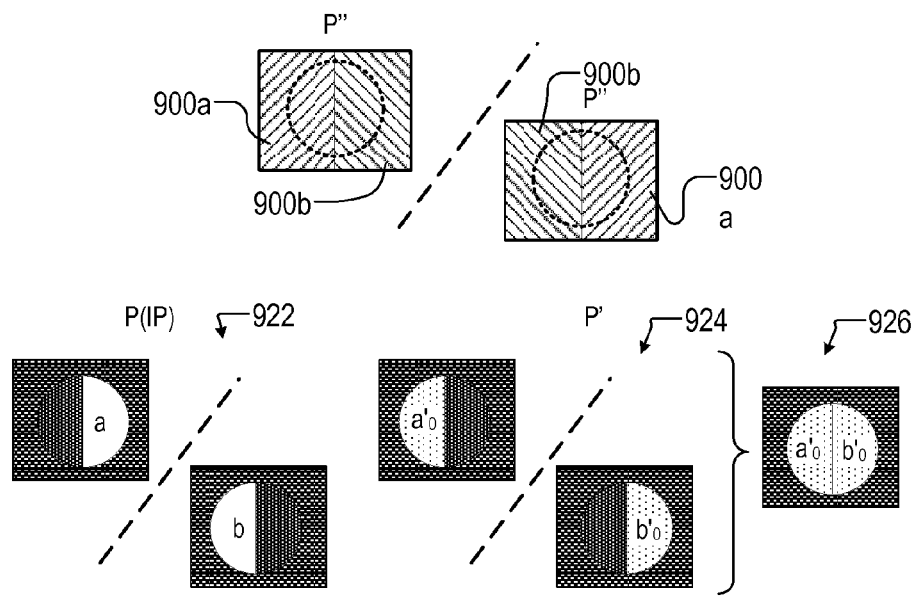
FIG. 10 illustrates in more detail operation of the apparatus of FIG. 10 to measure zero order diffracted radiation by a switching mode of operation.

FIG. 10 illustrates a switching mode of operation, for use in cases where zero order scattered radiation for the whole pupil is desired. Two pupil images are captured by detector 19, using different settings of the array 942. In a first setting, mirror elements in a left half 900a of the array are set to the first position and elements in the right half 900b are set to the second position. After a sufficient measurement time, a first image is stored and the settings of the two halves are switched so that elements 900a and in the right half and elements 900b are in the left half. A second image is captured, with identical capture settings as the first image. The two images therefore contain measurement data for two complementary spatial profiles of illumination and two complementary spatial profiles of collection.

At 922 the two complementary illumination profiles are shown, in which firstly the right half of the pupil is bright (region a) and then secondly the left half of the pupil is bright. At 924 we see the captured images of the scattered zero order radiation. From these two captured images, a complete measurement of zero order scattering across the pupil is generated at 926. Now, it will be appreciated that two image capture operations take twice as long as a single capture. Remembering, however, that the captured images are four times as bright in the present apparatus as in the known apparatus, the overall capture time, even for this two-capture mode of operation, is no worse than in the known apparatus. For other modes of operation, such as that illustrated in FIG. 9, operating speed can be greatly increased (and/or measurement quality can be increased without decreasing speed).

Following these examples, it can be seen how zero and/or non-zero order scattered radiation can be collected and measured, to perform angle-resolved scatterometry and diffraction based measurements of the same types as in the known apparatus. Signal strength is maximized, compared with arrangements reliant on beam splitters and/or LC shutters. Measurements with different polarizations and wavelengths can be taken as desired.

Figure 11:
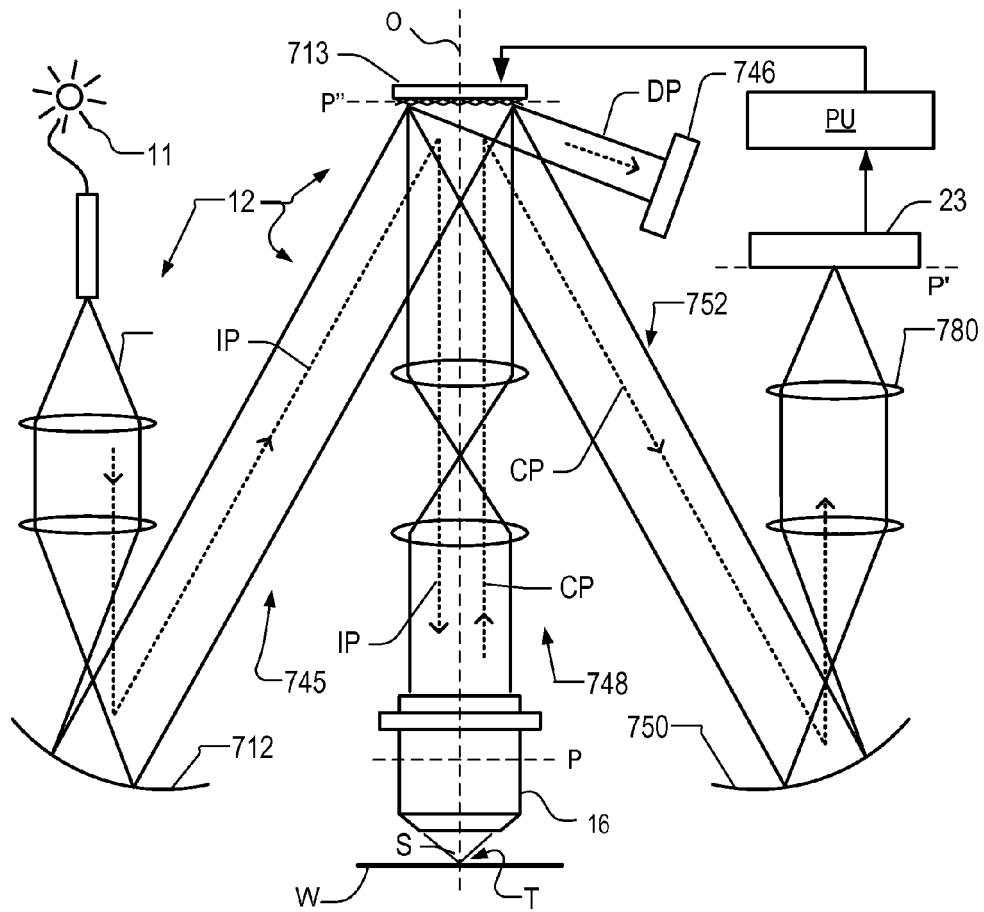
FIG. 11 is a schematic view of an inspection apparatus adapted to perform angle-resolved scatterometry and dark-field imaging inspection methods according to a second embodiment of the present invention.

FIG. 11 is a schematic view of an inspection apparatus adapted to perform dark-field imaging inspection methods according to a second embodiment of the present invention. The apparatus is identical to that of FIG. 7, except that an field image sensor 23 is provided instead of a pupil image sensor 19. Additional optical elements 780 focus an image of the target T onto the sensor 23. Sensor 23 is thereby located in a field plane F' conjugate with the plane of target T, rather than in a pupil plane. All the functions of the dark-field imaging branch of the known apparatus can be implemented.

As already mentioned, the present disclosure does not exclude the provision of beam splitters to split the radiation into different functional branches. Accordingly, in a third embodiment of the present disclosure the apparatuses of FIGS. 7 and 11 are combined in a single apparatus in the same way as they are in the known apparatus of FIG. 5, using a beam splitter 17.

Application Example

Figure 12:
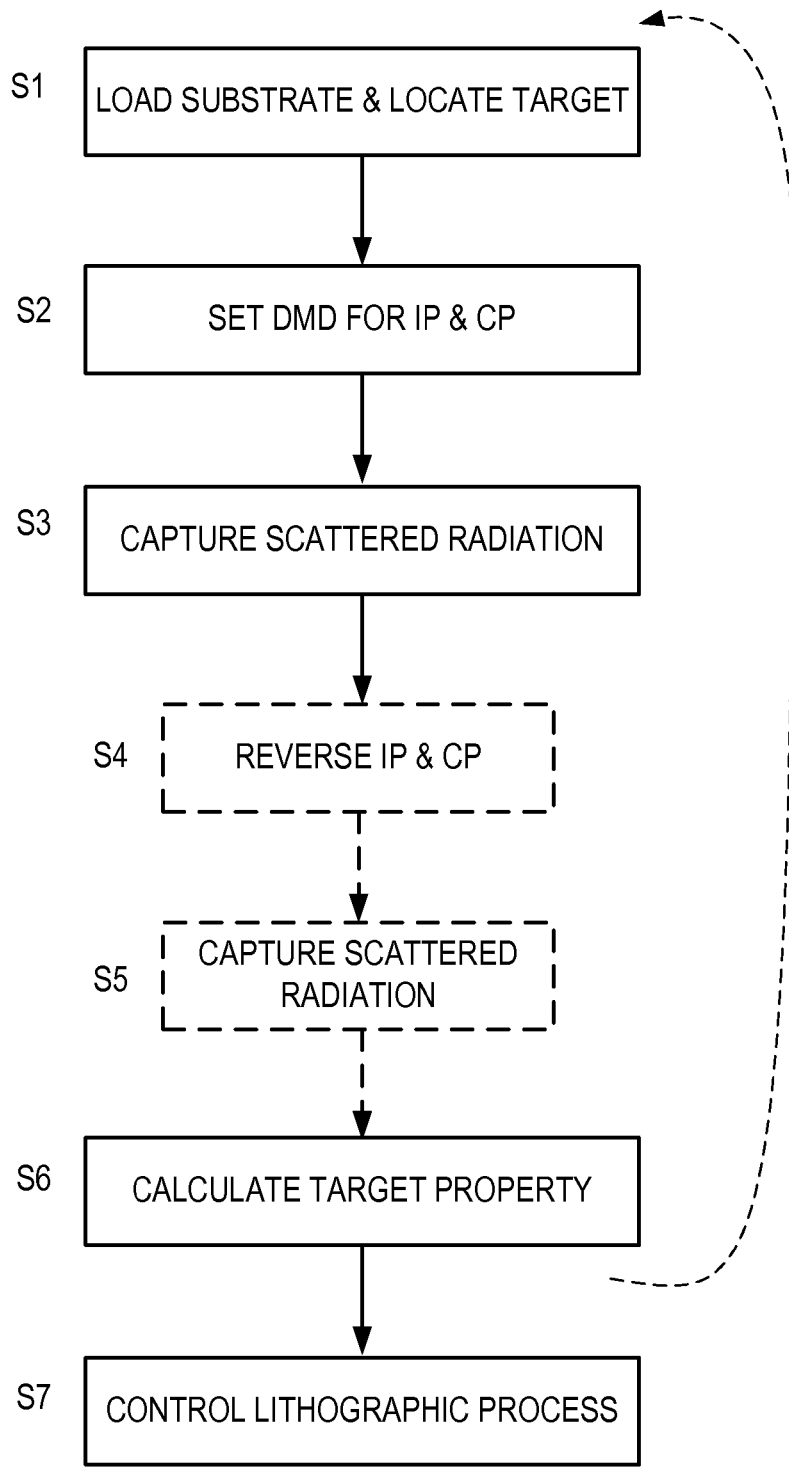
FIG. 12 is a flowchart of a method of controlling a lithographic process using an inspection apparatus according to an embodiment of the present invention.

FIG. 12 is a flowchart showing the application of the inspection apparatus of the above embodiments in monitoring and control of a lithographic process in the manufacture of devices. In step S1 a substrate W is loaded into the inspection apparatus. The substrate has one or more target structures that have been formed by the lithographic process. A target T is located in the field of view of the optical system, for example beneath objective lens 16. In step S2, the mirror array device 713 is set into desired configuration, with different mirror elements being positioned to define active areas of the illumination path IP and collection path CP. Optionally, of course, configurations having third positions may be implemented, as discussed above.

In step S3, the inspection apparatus is operated to capture scattered radiation using the defined configuration. Referring to the example of FIG. 10, optional steps S4 and S5 may be performed to capture images using a reversed configuration of paths IP and CP.

In step S6, a property of the target is calculated using the scattered radiation, using any of the techniques described in the prior applications cited in the introduction above. In step S7 the calculated target properties are used in the control of the lithographic process. For example, where the calculated property is overlay, corrections may be included in alignment models used in processing subsequent substrates, and/or in subsequent processing of the same substrate.

It will be understood in this regard that the method in practice may be performed on several different targets at a given location on the substrate, and at several target locations across substrate W, to obtain the desired information. Two or more measurements on the same target may be performed, for example using different wavelengths (colors) and/or different polarizations of illuminating radiation.

The implementation shown in FIGS. 7 to 12 is not the only one possible and many variants can be considered. Already some variants have been mentioned above.

Generally speaking, when using a mirror array device, each mirror element (pixel) must be either active or not active in the illumination path. Pixels 'half active' are not available. In case partially active pixels are desired in the illumination profile, this can be done in DMD devices by switching a pixel on and off rapidly during capture. In an embodiment where each mirror element has only two positions, the utility of this is limited because the same pixel would be partially active in both the illumination path and collection path. However, this effect only applies when the switching is integrated over an image capture period. The two paths would never in fact be active at the same time.

The present disclosure does not exclude the possibility that aperture devices additional to the mirror array device are include in one or both of the illumination path and the collection path.

Conclusion

The inspection apparatuses disclosed herein can eliminate sources of delay and/or error that are associated with mechanical switching of illumination parameters and illumination profiles. The inspection apparatuses can use more of the source radiation, thereby to make more measurements in a given time, and/or to make measurements with improved signal to noise ratios. Optimized spatial profiles allow better metrology performance, whether in scatterometry, diffraction based metrology, dark-field imaging metrology or other techniques. Improved speed of switching between illumination recipes allows certain types of measurement to be undertaken more quickly, particularly when a single measurement such as asymmetry requires more than one measurement on the same target, or when it is desired to make different measurements on several targets at locations across a substrate. Improved performance in metrology yields improved performance in the lithographic process, when corrections are applied based on measurement results obtained with the inspection apparatus.

A method of manufacturing devices using the lithographic process can be improved by providing an inspection apparatus as disclosed herein, using it to measure processed substrates to measure parameters of performance of the lithographic process, and adjusting parameters of the process to improve or maintain performance of the lithographic process for the processing of subsequent substrates.

In association with the physical grating structures of the targets as realized on substrates and patterning devices, an embodiment may include a computer program containing one or more sequences of machine-readable instructions describing a methods of designing metrology recipes and/or controlling the inspection apparatus to implement the spatial profile of illumination and the spatial profile of collection and other aspects of those metrology recipes. This computer program may be executed for example in a separate computer system employed for the design/control process. Alternatively, the process may be wholly or partly performed within unit PU in the apparatus of FIG. 7 and/or the control unit LACU of FIG. 2. There may also be provided a data storage medium (e.g., semiconductor memory, magnetic or optical disk) having such a computer program stored therein.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the invention are provided in below numbered clauses:

1. An inspection apparatus comprising:
   an illumination system for illuminating a target structure with illuminating radiation;
   a collection system for collecting the illuminating radiation after it has been scattered by the target structure; and
   a programmable spatial light modulator that forms part of both the illumination system and the collection system, the spatial light modulator comprising an array of movable reflective elements and being operable to define simultaneously a spatial profile of the illuminating radiation and a spatial profile of collection of the scattered radiation.

2. An inspection apparatus according to clause 1 further comprising an objective lens that forms part of both the illumination system and the collections system, and wherein the array of movable mirror elements is provided in a plane conjugate with a pupil plane of the objective lens.

3. An inspection apparatus according to clause 2 wherein the collection system includes an image detector provided in another plane conjugate with the pupil plane of the objective lens.

4. An inspection apparatus according to clause 2 or 3 wherein the collection system includes an image detector provided in a plane conjugate with a field plane of the objective lens.

5. An inspection apparatus according to any preceding clause wherein each element in the array of reflective elements is movable between at least a first position and a second position, and wherein reflective elements that are in the first position define active portions of the spatial profile of the illuminating radiation while elements that are in the second position define active portions of the spatial profile of collection.

6. An inspection apparatus according to clause 5 wherein at least one of the reflective elements is further movable to a third position in which it defines neither an active portion of the spatial profile of the illuminating radiation nor an active portion of the spatial profile of collection.

7. An inspection apparatus according to clause 5 or 6 wherein between the array of reflective elements and the target a common optical path is defined forming part of the illumination system and the collection system, and wherein each element in the array of reflective elements when in the first position is oriented so as to reflect radiation from an illumination input path into the common optical path and when in the second position is oriented to reflect radiation from the common optical path into an output path.

8. An inspection apparatus according to clause 7 wherein each element in the array of reflective elements when in the second position is oriented so as to reflect radiation from the illumination input path into a beam dump.

9. An inspection apparatus according to clause 6 wherein each element in the array of reflective elements when in the second position is oriented so as to reflect radiation from the illumination input path into an auxiliary sensor.

10. An inspection apparatus according to clause 7, 8 or 9 wherein the illumination system includes an illumination path folding mirror for delivering the illuminating radiation from a radiation source into the illumination input path.

11. An inspection apparatus according to clause 9 wherein the illumination path folding mirror is curved.

12. An inspection apparatus according to clause 7, 8, 9 or 10 wherein the illumination system includes a collection path folding mirror for delivering radiation from the output path to a detector.

13. An inspection apparatus according to clause 12 wherein the collection path folding mirror is curved.

14. An inspection apparatus according to any preceding clause further comprising a controller for receiving signals specifying a desired spatial profile and for setting the positions of the reflective elements to implement the specified profile.

15. An inspection apparatus according to any preceding clause further comprising a processor arranged to receive measurement data from the collection system and to use the received measurement data in combination with knowledge of the spatial profile of illumination and the spatial profile of collection to calculate a property of the target structure.

16. An inspection apparatus according to clause 15 wherein said processor is arranged to receive measurement data obtained using two complementary combinations of spatial profile of illumination and spatial profile of collection and to use the received measurement data in combination with knowledge of the spatial profiles of illumination and the spatial profiles of collection to calculate a property of the target structure.

17. An inspection apparatus according to any preceding clause further comprising a processor arranged to receive the calculated property of the target structure and to generate corrections for use in controlling future performance of a lithographic process by which the target structure was made.

18. A method of inspection of a target structure comprising:
  illuminating a target structure with illuminating radiation;
  collecting the illuminating radiation after it has been scattered by the target structure;
  using a programmable spatial light modulator that comprises an array of movable mirror elements to define simultaneously a spatial profile of the illuminating radiation and a spatial profile of collection of the scattered radiation.

19. A method according to clause 18 wherein an objective lens is used in both the illumination and the collection steps, and wherein the array of movable mirror elements is provided in a plane conjugate with a pupil plane of the objective lens.

20. A method according to clause 19 further comprising capturing part of the collected scattered radiation using an image detector provided in another plane conjugate with the pupil plane of the objective lens.

21. A method according to clause 19 or 20 further comprising capturing part of the collected scattered radiation using an image detector provided in a plane conjugate with a field plane of the objective lens.

22. A method according to any of clauses 18 to 21 wherein each element in the array of reflective elements is movable between at least a first position and a second position, and wherein reflective elements that are in the first position define active portions of the spatial profile of the illuminating radiation while elements that are in the second position define active portions of the spatial profile of collection.

23. A method according to any of clauses 18 to 22 further comprising generating or receiving signals specifying a desired spatial profile and setting the positions of the reflective elements to implement the specified profile.

24. A method according to any of clauses 18 to 23 further comprising generating or receiving signals specifying a desired spatial profile and setting the positions of the reflective elements to implement the specified profile.

25. A method according to any of clauses 18 to 24 further comprising receiving measurement data from the collection system and using the received measurement data in combination with knowledge of the spatial profile of illumination and the spatial profile of collection to calculate a property of the target structure.

26. A method according to clause 25 wherein measurement data is obtained using two complementary combinations of spatial profile of illumination and corresponding spatial profiles of collection.

27. A method of manufacturing devices wherein a device pattern is applied to a series of substrates using a lithographic process, the method including:
  using a method according to clause 25 or 26 to measure a property of at least one structure of interest formed on at least one of said substrates, and
  controlling the lithographic process for later substrates in accordance with the measured property.

28. A method of manufacturing devices wherein a device pattern is applied to a series of substrates using a lithographic process, the method including:
  using an inspection apparatus according to clause 15 or 16 to measure a property of at least one structure of interest formed on at least one of said substrates, and
  controlling the lithographic process for later substrates in accordance with the measured property.

29. A computer program product comprising machine-readable instructions for causing a processor to control the array of reflective elements in an inspection apparatus according to any of clauses 1 to 16, thereby to implement a plurality of spatial profiles of illumination and associated spatial profiles of collection to calculate a property of the target structure.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An inspection apparatus comprising:
an illumination system comprising a radiation source and a programmable spatial light modulator and configured to illuminate a target structure with an illuminating radiation;
a collection system comprising the programmable spatial light modulator and configured to collect the illuminating radiation after it has been scattered by the target structure and to deliver the scattered radiation to an image detector; and
the programmable spatial light modulator comprising an array of movable reflective elements and being configured to define simultaneously a spatial profile of the illuminating radiation and a spatial profile of collection of the scattered radiation,
wherein an element in the array of movable reflective elements, which is used in the illumination system, is not substantially simultaneously used in the collection system.

2. The inspection apparatus of claim 1, further comprising:
an objective lens that forms part of both the illumination system and the collection system, wherein the array of movable mirror elements is provided in a plane conjugate with a pupil plane of the objective lens.

3. The inspection apparatus of claim 2, wherein the image detector is provided in another plane conjugate with the pupil plane of the objective lens.

4. The inspection apparatus of claim 2, wherein the image detector is provided in a plane conjugate with a field plane of the objective lens.

5. The inspection apparatus of claim 1, wherein:
each element in the array of reflective elements is movable between at least a first position and a second position, and
reflective elements that are in the first position define active portions of the spatial profile of the illuminating radiation, while elements that are in the second position define active portions of the spatial profile of collection.

6. The inspection apparatus of claim 1, further comprising:
a controller configured to receive signals specifying a desired spatial profile and to set positions of the movable reflective elements to implement the specified profile.

7. The inspection apparatus of claim 1, further comprising:
a processor configured to receive measurement data from the image detector and to calculate a property of the target structure based on the received measurement data.

8. The inspection apparatus of claim 7, wherein the processor is configured to receive the measurement data obtained using two complementary combinations of the spatial profile of illumination and the spatial profile of collection and to calculate the property of the target structure based on the received measurement data.

9. The inspection apparatus of claim 1, further comprising:
a processor configured to receive a calculated property of the target structure and to generate corrections for use in controlling subsequent performance of a lithographic process by which the target structure was made.

10. A method of inspection of a target structure comprising:
using a programmable spatial light modulator that comprises an array of movable mirror elements to define simultaneously a spatial profile of an illuminating radiation and a spatial profile of collection of a scattered radiation;
illuminating a target structure with the illuminating radiation, wherein the illuminating comprises reflecting, using the programmable spatial light modulator, the illuminating radiation toward the target structure; and
collecting the illuminating radiation after it has been scattered by the target structure, wherein the collecting comprises reflecting, using the programmable spatial light modulator, the scattered radiation toward an image detector,
wherein an element in the array of movable mirror elements, which is used in the illuminating the target structure, is not substantially simultaneously used in the collecting the illuminating radiation.

11. The method of claim 10, wherein:
the illuminating and the collecting further comprise using an objective lens, and
the array of movable mirror elements is provided in a plane conjugate with a pupil plane of the objective lens.

12. The method of claim 11, further comprising:
capturing part of the collected scattered radiation using the image detector provided in another plane conjugate with the pupil plane of the objective lens.

13. The method of claim 11, further comprising:
capturing part of the collected scattered radiation using the image detector provided in a plane conjugate with a field plane of the objective lens.

14. The method of claim 10, wherein:
each element in the array of movable mirror elements is movable between at least a first position and a second position, and
movable mirror elements that are in the first position define active portions of the spatial profile of the illuminating radiation, while elements that are in the second position define active portions of the spatial profile of collection.

15. The method of claim 10, further comprising:
generating or receiving signals specifying a desired spatial profile; and
setting positions of the movable mirror elements to implement the specified profile.

16. The method of claim 10, further comprising:
receiving measurement data; and
calculating a property of the target structure based on the received measurement data.

17. The method of claim 16, wherein the measurement data is obtained using two complementary combinations of spatial profiles of illumination and corresponding spatial profiles of collection.

18. A method of manufacturing devices wherein a device pattern is applied to a series of substrates using a lithographic process, the method comprising:
calculating a property of at least one structure of interest formed on at least one of the substrates, the calculating comprising:
using a programmable spatial light modulator that comprises an array of movable mirror elements to define simultaneously a spatial profile of an illuminating radiation and a spatial profile of collection of a scattered radiation;
illuminating the at least one structure with the illuminating radiation, wherein the illuminating comprises reflecting, using the programmable spatial light modulator, the illuminating radiation toward the target structure;
collecting the illuminating radiation after it has been scattered by the at least one structure, wherein the collecting comprises reflecting, using the programmable spatial light modulator, the scattered radiation toward an image detector,
wherein an element in the array of movable mirror elements, which is used in the illuminating the at least one structure, is not substantially simultaneously used in the collecting the illuminating radiation;
receiving, by the image detector, the collected scattered radiation and generating measurement data based on the received collected scattered radiation; and
calculating, using a processor, the property of the at least one structure, based on the measurement data; and
controlling the lithographic process for subsequent substrates based on the calculated property.

19. A non-transitory computer program product comprising machine-readable instructions for causing a processor to perform operations comprising:
controlling a programmable spatial light modulator, wherein:
the programmable spatial light modulator foul's part of an illumination system and the programmable spatial light modulator forms part of a collection system, the collection system configured to collect an illuminating radiation after it has been scattered by a target structure,
the programmable spatial light modulator comprises an array of movable reflective elements and is configured to define simultaneously a spatial profile of the illuminating radiation and a spatial profile of collection of a scattered radiation,
the controlling implements a plurality of spatial profiles of illumination and associated spatial profiles of collection, and
an element in the array of movable reflective elements, which is used in the illumination system, is not substantially simultaneously used in the collection system;
receiving measurement data, wherein the measurement data is generated based on the collected scattered radiation; and
calculating a property of the target structure based on the measurement data.

* * * * *